US008603036B2

(12) United States Patent
Parker

(10) Patent No.: US 8,603,036 B2
(45) Date of Patent: Dec. 10, 2013

(54) VASCULAR INTRODUCER AND METHOD OF USING SAME

(75) Inventor: Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/162,686

(22) Filed: Jun. 17, 2011

(65) Prior Publication Data

US 2012/0004610 A1 Jan. 5, 2012

Related U.S. Application Data

(60) Provisional application No. 61/360,625, filed on Jul. 1, 2010.

(51) Int. Cl.
*A61M 5/178* (2006.01)
*A61M 31/00* (2006.01)

(52) U.S. Cl.
USPC ......................... 604/164.1; 604/158; 604/508

(58) Field of Classification Search
USPC ......... 604/164.1, 158–170.03, 198, 246, 264, 604/508
See application file for complete search history.

(56) References Cited

U.S. PATENT DOCUMENTS 3,421,509 A 1/1969 Fiore
4,772,260 A 9/1988 Heyden
4,863,440 A 9/1989 Chin
4,963,137 A 10/1990 Heyden
6,458,147 B1 * 10/2002 Cruise et al. .................. 606/214
6,585,721 B2 7/2003 Fiore
7,255,687 B2 8/2007 Huang et al.
7,425,202 B2 9/2008 Huang et al.
7,604,621 B2 10/2009 Eidenschink
2001/0044595 A1 11/2001 Reydel et al.
2006/0173422 A1 8/2006 Reydel et al.

FOREIGN PATENT DOCUMENTS

WO WO 2004096335 A1 * 11/2004

* cited by examiner

*Primary Examiner* — Nicholas Lucchesi
*Assistant Examiner* — Niyati D Shah
(74) *Attorney, Agent, or Firm* — Liell & McNeil

(57) ABSTRACT

A vascular introducer for accessing a circulatory system of a patient includes a sheath and a dilator. The sheath includes a fitting attached at a proximal end, and includes a liner that is longer than a core tube. A proximal segment of the liner is attached to an inner surface of the core tube, but a distal segment of the liner is everted to cover an outer surface of a distal segment of the core tube. The dilator is positioned in the sheath and includes a tapered distal segment that extends beyond a distal end of the sheath. A handle is attached to the proximal end of the dilator and extends proximally from the fitting. During a procedure, a blood vessel may constrict and grip the sheath. During withdrawal of the sheath, the core tube is slid within a first portion of the everted distal segment of the liner while another portion of the liner is de-everting.

18 Claims, 2 Drawing Sheets

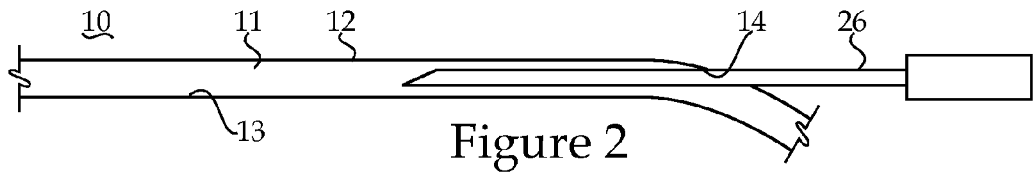
Figure 2
Figure 3
Figure 4
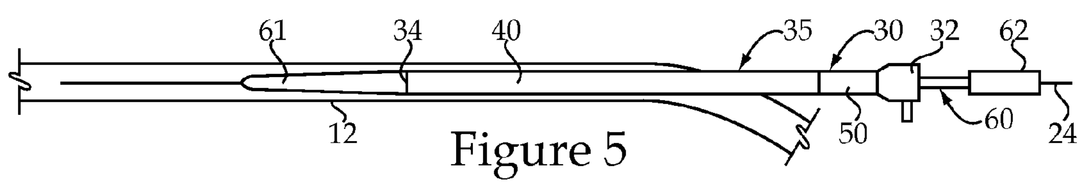
Figure 5
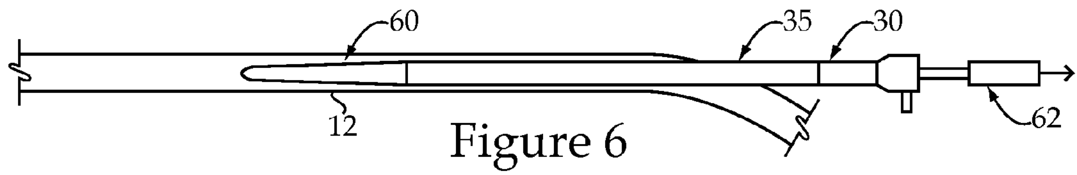
Figure 6
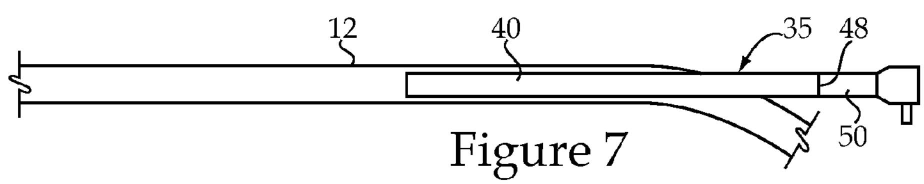
Figure 7
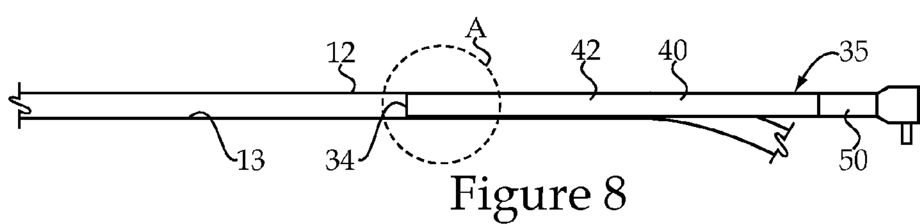
Figure 8
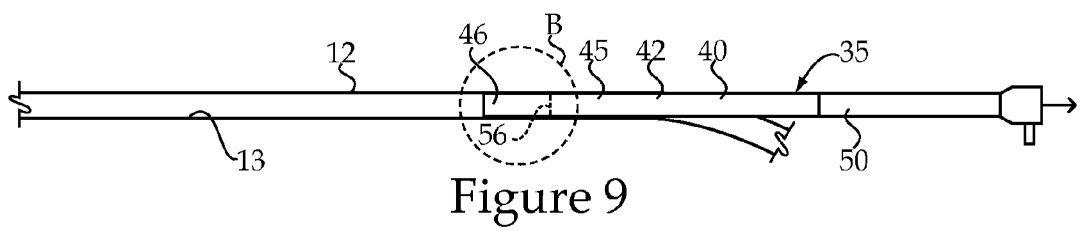
Figure 9

VASCULAR INTRODUCER AND METHOD OF USING SAME

RELATION TO OTHER PATENT APPLICATION

This application claims priority to provisional patent application Ser. No. 61/360,625, filed Jul. 1, 2010 with the same title.

TECHNICAL FIELD

The present disclosure relates generally to vascular introducers for percutaneous access to a patient's circulatory system, and more particularly to a vascular introducer that includes a sheath with a liner everted back over a portion of a core tube.

BACKGROUND

Gaining access to a patient's circulatory system to perform some treatment has long been known using the Seldinger technique. In recent years, this same technique has been used to gain access to smaller arteries, such as the radial artery, in the limb extremities. Although many percutaneous devices, such as vascular introducers, have been shown to scale in order to provide access to these smaller diameter arteries, new problems have developed that appear to be only related to smaller arteries. For instance, after the vascular introducer has been inserted into the circulatory system, some procedure may be performed, such as dilation of another location with a balloon catheter. In some instances, during the procedure, the small artery can tend to constrict and grip the outer surface of the sheath of the vascular introducer, making its withdrawal from the patient more difficult after the procedure is performed. In other words, due to the constriction of the artery, substantial friction can be created between the outer surface of the sheath and the blood vessel wall, which can make withdrawal of the sheath difficult and may lead to trauma to the inner surface of the blood vessel wall.

The present disclosure is directed toward overcoming one or more of the problems set forth above.

SUMMARY OF THE DISCLOSURE

In one aspect, a vascular introducer for accessing a circulatory system of the patient includes a sheath and a dilator. The sheath has a fitting attached to a proximal end, and includes a liner that is longer than a core tube. A proximal segment of the liner is attached to an inner surface of the core tube, while a distal segment of the liner is everted to cover an outer surface of a distal segment of the core tube. The dilator is positioned in the sheath and includes a tapered distal segment extending beyond a distal end of the sheath. A handle is attached to a proximal end of the dilator and extends proximally away from the fitting.

In another aspect, the vascular introducer is a portion of a kit that also includes a wire guide and an access needle all positioned together in a sterile peel open package.

In still another aspect, a method of treating a patient includes puncturing an opening through a blood vessel wall into a circulatory system of the patient with a needle. A wire guide is slid through the needle into the circulatory system, and the needle is withdrawn leaving the wire guide in place. A vascular introducer is slid over the wire guide through the blood vessel wall and into the circulatory system while a distal segment of a liner remains everted to cover a distal segment of a core tube. After withdrawing the wire guide, the dilator is decoupled from a sheath of the vascular introducer by withdrawing the dilator through a proximal segment of the liner of the sheath. The sheath is withdrawn by sliding the core tube within a first portion of the everted distal segment of the liner while de-everting another portion of the distal segment of the liner.

BRIEF DESCRIPTION OF THE DRAWINGS

FIG. 2 is a side view of an access needle inserted into a blood vessel of a patient;

FIG. 3 is a view similar to FIG. 2 after a wire guide has been inserted into the blood vessel through the access needle;

FIG. 4 is a view similar to FIG. 3 after the access needle has been withdrawn;

FIG. 5 is a view similar to FIG. 4 after a vascular introducer has been slid over the wire guide into the blood vessel;

FIG. 6 is a side view similar to FIG. 5 after the wire guide has been withdrawn;

FIG. 7 is a side view of the sheath of vascular introducer of FIG. 6 after the dilator has been withdrawn;

FIG. 8 is a view similar to FIG. 7, except after the blood vessel has constricted to grip the sheath;

FIG. 9 is a view similar to FIG. 8 showing the sheath being withdrawn from the patient.

DETAILED DESCRIPTION

Figure 1:
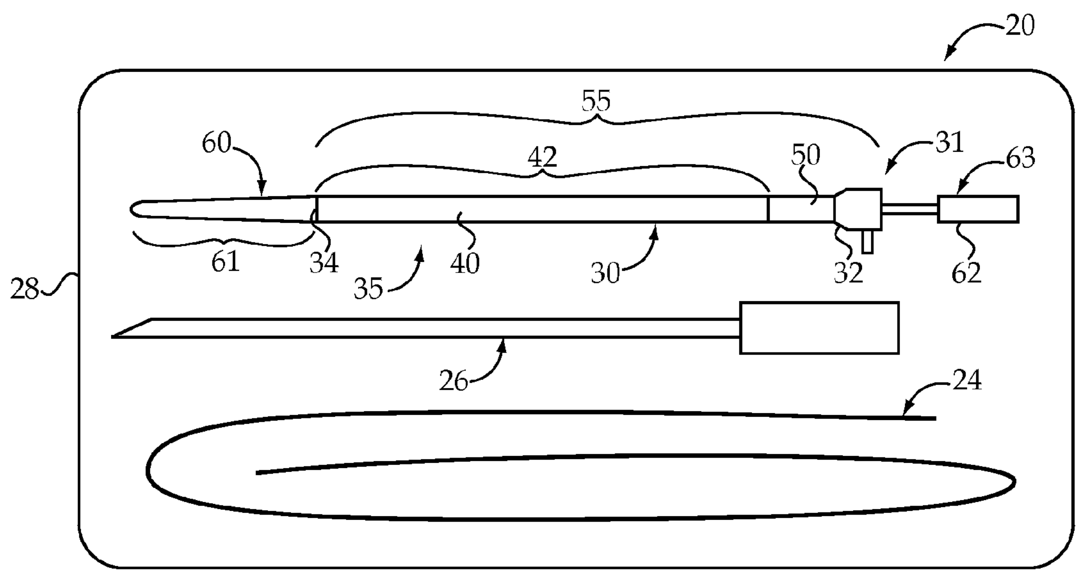
FIG. 1 is a top view of a vascular introducer kit according to one aspect of the present disclosure.

Referring to FIG. 1, a vascular introducer kit 20 includes a vascular introducer 30, a wire guide 24 and an access needle 26 all positioned together in a peel-open package 28, which may be sterile or ready to be sterilized at another location. Vascular introducer 30 includes a sheath 35 and a dilator 60. Sheath 35 and dilator 60 are shown in their pre-assembled condition as they would be prior to use with regard to treating a patient. Those skilled in the art will appreciate that the dilator 60 is received in a central lumen of the sheath 35, and itself defines a wire guide passage extending its complete length in a conventional manner. As shown, dilator 60 is positioned in sheath 35 and includes a tapered distal segment 61 extending beyond a distal end 34 of the sheath 35. In addition, dilator 60 includes a handle 62 attached to a proximal end 63 and extending proximally away from a fitting 32 at the proximal end 31 of sheath 35.

Figure 8A:
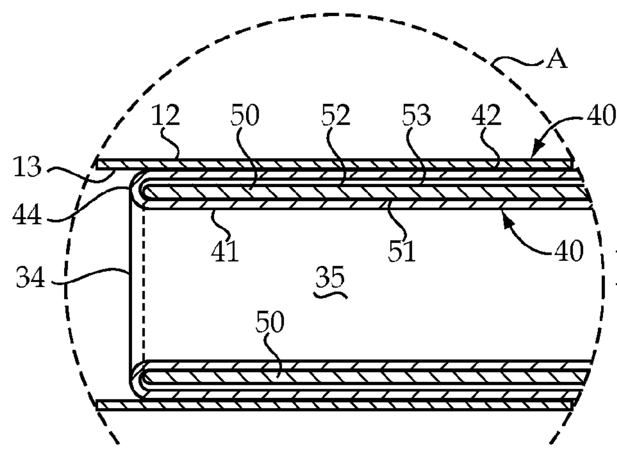
FIG. 8A is an enlarged view of detail A of FIG. 8.
Figure 9B:
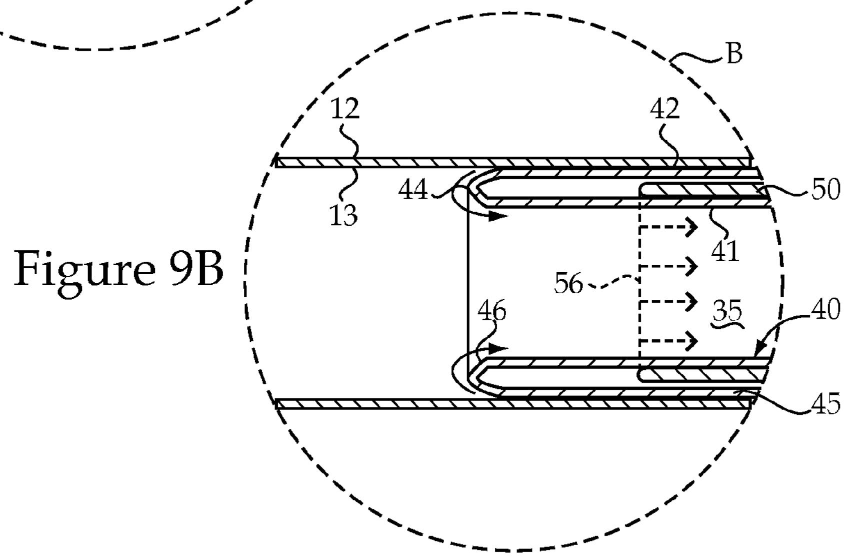
FIG. 9B is an enlarged view of detail B from FIG. 9.

Referring now in addition to FIGS. 8A and 9B, sheath 35 includes a liner 40 that is substantially longer than a core tube 50. A proximal segment 41 of liner 40 is attached to an inner surface 51 of core tube 50. A distal segment 42 of liner 40 may be everted to cover an outer surface 52 of a distal segment 53 of core tube 50. Liner 41 may be comprised of a fluoropolymer such as polytetrafluoroethylene, while core tube 50 may comprise a conventional thermoplastic such as nylon. Liner 40 may be substantially longer than core tube 50. For instance, in the case of a vascular introducer 30 for gaining access to small arteries, such as a radial artery, core tube 50 may have a length between 8 and 12 centimeters, and the liner 40 may be between 4 and 6 centimeters longer than core tube 50. In addition, in such a case, core tube 50 would have a diameter less than or equal to 6 French in order to accommodate the small diameter arteries. Proximal segment 41 of liner 40 may be continuously attached the entire length 55 of core tube 50. As best shown in FIGS. 8A and 9B, the distal segment 42 of liner 40 may be in contact with, but unattached to, the outer surface 52 of the distal segment 53 of core tube 50.

Sheath 35 may be constructed using known techniques. For instance, a tube segment of liner 40 may be slid over a mandrel, which is then slid inside of a raw core tube segment. A shrink wrap tube may then be slid over the outer surface of the core tube segment, and the tube is then heated to form a continuous bonding attachment between an outer surface of the proximal segment 41 of liner 40 with the inner surface 51 of core tube 50 in a conventional manner. After that portion of sheath 35 is constructed, the distal segment 42 of liner 40 may be everted to cover the outer surface 52 of core tube 50. At some point during this construction, the fitting 32 would be attached to the proximal end 31 of sheath 30. Next, the construction would be completed by mating a dilator 60 to sheath 35 in a conventional manner. Liner 40 may have a relatively smooth inner surface to better facilitate sliding interaction with other medical devices, such as balloon catheters, wire guides or the like used for administering a treatment in the circulatory system of the patient. On the other hand, the exterior surface of liner 40 may have texturing to better facilitate bonding with the thermoplastic of core tube 50. Although not shown, a re-enforcement layer, such as a metallic coil and/or braid, may be positioned between the proximal segment 41 of liner 40 and the core tube 50.

Industrial Applicability

The present disclosure finds general applicability in any vascular introducer for gaining access to the circulatory system of a patient. The present disclosure finds particular application in smaller diameter vascular introducers for use in smaller arteries that tend to constrict while the introducer is in situ within the patient, making withdrawal of the device more difficult. Thus, the vascular introducer of the present disclosure may find particular applicability in, for instance, as a radial artery introducer. Nevertheless, the concepts associated with the present disclosure could find potential application in any introducer in which the patient's tissue tends to constrict and grip the outer surface of the introducer some time after initial placement making withdrawal of the device more difficult.

Referring now in addition to FIGS. 1-9B, a method of treating a patient 10 is illustrated using the vascular introducer 30 of the present discloser in conjunction with a typical Seldinger technique. In particular, the procedure may begin by puncturing an opening 14 through a blood vessel 13 into the circulatory system 11 of patient 10 with an access needle 26 as shown in FIG. 2. Next, a wire guide 24 may be slid through the needle 26 into the circulatory system 11 as shown in FIG. 3. The needle 26 may then be withdrawn leaving the wire guide 24 in place as shown in FIG. 4. Next, the vascular introducer 30 may be slid over wire guide 24, through the blood vessel wall 13 and into blood vessel 12 as shown in FIG. 5. During this portion of the procedure, the liner 40, the core tube 50 and the dilator 60 may maintain a fixed spatial relationship relative to each other. After vascular introducer 30 has been properly positioned in blood vessel 12, the wire guide 24 may be withdrawn as shown in FIG. 6. Next, the dilator 60 may be decoupled from sheath 35 and withdrawn from the patient leaving sheath 35 in place as shown in FIG. 7. Between FIGS. 7 and 8, some suitable procedure may be performed on patient 10. For instance, a balloon catheter (not shown) may be introduced through sheath 35 to a remote location in the patient's circulatory system 11 to, for instance, dilate an occlusion. While the sheath 35 is in place, blood vessel 12 may constrict around the vascular introducer and grip the outer surface of sheath 35 prior to its withdrawal from the patient 10. Although not necessary, and depending upon a choice of lengths for the liner 40 and core tube 50, the liner 40 may be sufficiently long that it actually isolates the core tube 50 from patient 10 by enclosing a segment of core tube 50 that is positioned within liner 40 and the patient 10, as shown in FIG. 7.

Nevertheless, liner 40 may be shorter than that shown such that its distal end 48 is also positioned within patient 10, without departing from the intended scope of the present disclosure.

Referring now in addition to FIGS. 8A and 9B, prior to withdrawal from the patient, the distal end 56 of core tube 50 may provide the turn around eversion corner 44 for liner 40 as shown in FIG. 8A. In the past, because the blood vessel 12 has constricted around to grip sheath 35, its withdrawal from the patient can be met with increased friction creating problems and also potentially causing trauma to the inner wall of blood vessel 12. In order to accommodate this difficulty, the sheath 35 may be withdrawn by pulling on fitting 32 and sliding core tube 50 within a first portion 45 of the everted distal segment 42 of liner 40, while another portion 46 of the distal segment 42 of liner 40 is de-everting as shown in FIG. 9B. This action has sometimes been referred to as roll sock, because it resembles the action of a sock everted on itself that is unrolling to extend its length by being de-everted. Depending upon the length of distal segment 42 of liner 40, the sheath may have a post use configuration in which the liner becomes completely de-everted such that the entire distal segment 42 of liner 40 is de-everted around moving eversion corner 44 and extends distally away from the distal end of core tube 50.

Thus, when sheath 35 is withdrawn from patient 10, there may not be any sliding interaction between the sheath and the inner surface 13 of the blood vessel 12. In addition, because the contact surface between distal segment 42 of liner 40 and the outer surface 53 of core tube 50 is low friction, the device may be easily withdrawn from the patient. In addition, the de-eversion of the distal segment 42 of liner 40 can also result in little to no sliding friction interaction with the blood vessel 12.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. A method of treating a patient with a vascular introducer for accessing a circulatory system of a patient, the vascular introducer comprising: a sheath with a fitting attached to a proximal end and including a liner that is longer than a core tube, and a proximal segment of the liner being attached to an inner surface of the core tube, and a distal segment of the liner being everted to cover an outer surface of a distal segment of the core tube; and a dilator positioned in the sheath and including a tapered distal segment extending beyond a distal end of the sheath, and a handle attached to a proximal end that extends proximally from the fitting, comprising the steps of:

puncturing an opening through a blood vessel wall into a circulatory system of the patient with a needle;

sliding a wire guide through the needle into the circulatory system;

withdrawing the needle while leaving the wire guide in place;

sliding the vascular introducer over the wire guide, through the blood vessel wall and into the circulatory system while the distal segment of the liner remains everted to cover the distal segment of the core tube;

withdrawing the wire guide;

decoupling a dilator from the sheath of the vascular introducer by withdrawing the dilator through the proximal segment of the liner of the sheath; and withdrawing the sheath, which includes the core tube and the liner, at least in part by sliding the core tube within a first portion of the everted distal segment of the liner while de-everting another portion of the distal segment of the liner.

2. The method of claim 1 including a step of gripping the sheath with increased friction against withdrawal after the vascular introducer sliding step, but before the sheath withdrawal step.

3. The method of claim 1 wherein the core tube is isolated from the patient during the vascular introducer sliding step through the sheath withdrawing step by enclosing a segment of the core tube within the liner.

4. The method of claim 3 including a step of gripping the sheath with increased friction against withdrawal after the vascular introducer sliding step, but before the sheath withdrawal step.

5. The method of claim 1 wherein the liner, the core tube and the dilator maintain a fixed spacial relationship between each other during the vascular introducer sliding step.

6. The method of claim 5 wherein the core tube is isolated from the patient during the vascular introducer sliding step through the sheath withdrawing step by enclosing a segment of the core tube within the liner; and including a step of gripping the sheath with increased friction against withdrawal after the vascular introducer sliding step, but before the sheath withdrawal step.

7. A vascular introducer for accessing a circulatory system of a patient, the vascular introducer comprising:

a sheath with a fitting attached to a proximal end and including a liner that is longer than a core tube, and a proximal segment of the liner being attached to an inner surface of the core tube, and a distal segment of the liner being everted to cover an outer surface of a distal segment of the core tube, and the distal segment of the liner being unattached to the distal segment of the core tube;

a dilator positioned in the sheath and including a tapered distal segment extending beyond a distal end of the sheath, and a handle attached to a proximal end that extends proximally from the fitting; and wherein the sheath had a post-use configuration in which the distal segment of the liner is de-everted and extends distally away from the distal end of the core tube.

8. The vascular introducer of claim 7 including a continuous attachment between the proximal segment of the liner and an entire length of the core tube.

9. The vascular introducer of claim 7 wherein the core tube and the liner are formed of different materials, with the core tube comprising a thermoplastic, but the liner comprises a fluoropolymer.

10. The vascular introducer of claim 9 wherein the fluoropolymer includes polytetrafluoroethylene; and the thermoplastic includes nylon.

11. The vascular introducer of claim 10 including a continuous attachment between the proximal segment of the liner and an entire length of the core tube.

12. The vascular introducer of claim 11 wherein the core tube has a length between eight and twelve centimeters; and the liner is between four and six centimeters longer than the core tube.

13. The vascular introducer of claim 12 wherein the core tube has a diameter less than or equal to six French.

14. A vascular introducer kit comprising:

a vascular introducer, a wire guide, and an access needle positioned in a peel-open package;

the vascular introducer including a sheath and a dilator;

the sheath having a fitting attached to a proximal end and including a liner that is longer than a core tube, and a proximal segment of the liner being attached to an inner surface of the core tube, and a distal segment of the liner being everted to cover an outer surface of a distal segment of the core tube, and the distal segment of the liner being unattached to the distal segment of the core tube;

the dilator being positioned in the sheath and including a tapered distal segment extending beyond a distal end of the sheath, and a handle attached to a proximal end that extends proximally from the fitting; and wherein the sheath has a post-use configuration in which the distal segment of the liner is de-everted and extends distally away from the distal end of the core tube.

15. The vascular introducer set of claim 14 wherein the core tube has a length between eight and twelve centimeters;

the liner is between four and six centimeters longer than the core tube; and the core tube has a diameter less than or equal to six French.

16. The vascular introducer set of claim 15 wherein the core tube and the liner are formed of different materials, with the core tube comprising a thermoplastic, but the liner comprising a fluoropolymer.

17. The vascular introducer set of claim 16 wherein the fluoropolymer includes polytetrafluoroethylene; and the thermoplastic includes nylon.

18. The vascular introducer set of claim 17 including a continuous attachment between the proximal segment of the liner and an entire length of the core tube.

* * * * *